United States Patent
Champagne et al.

(10) Patent No.: US 10,465,028 B2
(45) Date of Patent: Nov. 5, 2019

(54) POLYMER AS THICKENER AND SUSPENDING AGENT

(71) Applicant: COATEX, Genay (FR)

(72) Inventors: Clementine Champagne, Caluire-et-Cuire (FR); Delphine Bony, Quincieux (FR); Jean-Marc Suau, Lucenay (FR); Yves Kensicher, Theize (FR); Benoit Magny, Cailloux sur Fontaine (FR)

(73) Assignee: COATEX, Genay (FR)

( * ) Notice: Subject to any disclaimer, the term of this patent is extended or adjusted under 35 U.S.C. 154(b) by 30 days.

(21) Appl. No.: 15/737,862

(22) PCT Filed: Jun. 23, 2016

(86) PCT No.: PCT/FR2016/051537
§ 371 (c)(1),
(2) Date: Dec. 19, 2017

(87) PCT Pub. No.: WO2016/207554
PCT Pub. Date: Dec. 29, 2016

(65) Prior Publication Data
US 2019/0010267 A1    Jan. 10, 2019

(30) Foreign Application Priority Data

Jun. 23, 2015    (FR) ..................... 15 55751

(51) Int. Cl.
| | | |
|---|---|---|
| *C08F 220/18* | (2006.01) | |
| *A61K 8/81* | (2006.01) | |
| *A61K 8/86* | (2006.01) | |
| *A61Q 19/00* | (2006.01) | |
| *C08F 220/06* | (2006.01) | |
| *C08F 220/40* | (2006.01) | |
| *C08F 220/42* | (2006.01) | |
| *C08F 220/56* | (2006.01) | |
| *C08J 3/03* | (2006.01) | |
| *A61Q 19/10* | (2006.01) | |
| *C08F 222/10* | (2006.01) | |

(52) U.S. Cl.
CPC .......... *C08F 220/18* (2013.01); *A61K 8/8152* (2013.01); *A61K 8/86* (2013.01); *A61Q 19/00* (2013.01); *C08F 220/06* (2013.01); *C08F 220/40* (2013.01); *C08F 220/42* (2013.01); *C08F 220/56* (2013.01); *C08F 222/1006* (2013.01); *C08J 3/03* (2013.01); *A61K 2800/10* (2013.01); *A61K 2800/48* (2013.01); *A61Q 19/10* (2013.01); *C08F 2220/1808* (2013.01); *C08F 2220/1891* (2013.01); *C08F 2222/1026* (2013.01); *C08F 2800/20* (2013.01)

(58) Field of Classification Search
CPC .... C08F 220/18; C08F 220/06; C08F 220/40; C08F 220/42; C08F 220/56; C08F 222/1006; C08F 2220/1808; C08F 2220/1891; C08F 2222/1026; C08F 2800/20; A61K 8/8152; A61K 8/86; A61K 2800/10; A61K 2800/48; A61Q 19/00; A61Q 19/10
USPC ....................................... 526/329.5
See application file for complete search history.

(56) References Cited

U.S. PATENT DOCUMENTS

| | | | | |
|---|---|---|---|---|
| 4,309,330 | A * | 1/1982 | Ukita ................ | C08F 265/04 524/552 |
| 2012/0231056 | A1* | 9/2012 | Souzy ................ | A61K 8/068 424/401 |
| 2014/0112966 | A1 | 4/2014 | Souzy et al. | |

OTHER PUBLICATIONS

International Search Report dated Sep. 28, 2016 in PCT/FR2016/051537 filed Jun. 23, 2016.

* cited by examiner

*Primary Examiner* — Michael Bernshteyn
(74) *Attorney, Agent, or Firm* — Oblon, McClelland, Maier & Neustadt, L.L.P.

(57) ABSTRACT

The present invention relates to a polymer obtained by radical polymerization of a mixture of monomers comprising: at least one anionic monomer (a) having a polymerizable vinyl function; at least one non-ionic hydrophobic monomer (b) having a polymerizable vinyl function; and one or more crosslinking monomer(s) (c) including at least one compound of formula (I) in which R is a hydrogen atom or a methyl group, n is zero or an integer from 1 to 30, and $R_1$ is a linear or branched $C_1$-$C_{20}$ alkylene group. The present invention also relates to a process for the preparation thereof by radical polymerization, to an aqueous composition comprising same, to the use thereof as a thickener and suspending agent and also to the use of a monomer of formula (I) for synthesizing a polymer.

17 Claims, No Drawings

POLYMER AS THICKENER AND SUSPENDING AGENT

The present invention relates to novel polymers that may be used as rheology modifying agents for aqueous formulations and which can induce not only good thickening and clearness properties, but also good suspending performances.

Rheology modifying agents, also known as thickening agents or viscosity modifying agents, are present in cleaning compositions, whether this be in personal care or hygiene compositions, for example cosmetic compositions, or in maintenance compositions such as detergent products. These agents have an influence on the rheological properties (in particular viscosity) and esthetic properties (such as the clearness) of the formulation, which is generally rich in surfactants, and also on the capacity for suspending and stabilizing particles within the formulation.

Among the rheology modifying agents commonly used in aqueous formulations, mention may be made of alkali-soluble or swellable polymers, more commonly known by the abbreviation "ASE" (for "Alkali-Soluble or Swellable Emulsions") and hydrophobically-modified alkali-soluble or swellable polymers, more commonly known by the abbreviation "HASE" (for "Hydrophobically-modified Alkali-Soluble or Swellable Emulsions"). Thus, documents such as US2006/0271563, WO2014/090709 and CN104292378 describe aqueous compositions integrating polymers of this type as rheology modifying agents. Document U.S. Pat. No. 4,309,330 describes a copolymer in emulsion obtained from a dicyclopentadiene derivative, an unsaturated monomer, a hydroxylated unsaturated monomer and another monomer with an isocyanate function, which is useful for the preparation of a cross-linked coating. Document US 2012/0231056 describes a method for thickening a formulation by modifying its pH. This formulation is obtained from a copolymer prepared in direct emulsion and in the absence of cross-linking monomer.

Formulators are constantly in search of access to novel agents having the abovementioned properties and, as far as possible, improved properties in terms of performances, especially over a wide pH range.

The present invention aims precisely at satisfying these objects. Thus, it aims at proposing novel rheology modifying agents, which not only have good properties in terms of thickening effect (viscosity), but also make it possible to give formulations that have good suspending properties and high clearness (clear continuous phase), and which can do so over a wide pH range.

The inventors have discovered that it is possible to access to a formulation that satisfies all these criteria (viscosity, suspension performances and clearness) by using a specific polymer as rheology modifying agent. More particularly, the present invention relates, according to a first of its aspects, to a polymer obtained by radical polymerization of a mixture of monomers comprising:

at least one anionic monomer (a) having a polymerizable vinyl group, at least one nonionic hydrophobic monomer (b) having a polymerizable vinyl group and one or several cross-linking monomer(s) (c) including at least one compound of formula (I):

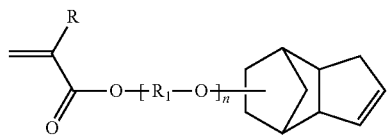

in which:
R is a hydrogen atom or a methyl group,
n is equal to 0 or is an integer from 1 to 30, for example from 1 to 20, or for example from 1 to 15, or for example from 1 to 10, and
$R_1$ is a $C_1$-$C_{20}$ linear or branched alkyl group.

Advantageously, as illustrated in the examples that follow, the polymers according to the invention give the aqueous formulation in which they are used good suspension, thickening and clearness properties, and do so over a wide pH range, i.e. equally well at acidic, neutral and basic pH values.

Typically, a polymer according to the invention is obtained by radical polymerization of a mixture of monomers comprising:

more than 20% by weight, based on the total weight of monomers forming the polymer of at least one anionic monomer (a) having a polymerizable vinyl group;

45% to 75% by weight, based on the total weight of monomers forming the polymer of at least one nonionic hydrophobic monomer (b) having a polymerizable vinyl group; and less than 5% by weight, based on the total weight of monomers forming the polymer of one or several cross-linking monomer(s) (c) including at least one compound of formula (I) as defined below.

The term "suspending properties" or "suspending power" is intended to denote the ability of the composition to maintain in suspension particles in its continuous phase, in particular stably over time, for example during storage of the composition.

For the purposes of the invention, the term "particles" to be suspended is intended to denote solid, filled or hollow bodies, but also liquid species that are immiscible with the continuous phase of the formulation or encapsulated or gaseous species which may be characterized by different shapes, textures, structures, compositions, colors and final properties. As a guide, mention may be made of exfoliant particles (for example polyethylene particles, pounded fruit shells or pumice), nourishing particles (for example collagen spheres), nacreous particles (for example mica titanium, glycol distearates) and esthetic particles (for example air bubbles, flakes or pigments, which are optionally colored). As regards the suspension of air bubbles in the composition, the particles may especially have a size of 1, 2 or 3 mm.

The suspension performances may be evaluated by applying a "suspension applicating test" by determining in particular the elastic modulus value G', the Tan (δ) value and the elastic resistance value, as described in the examples that follow.

The "clearness" or "clarity" of the composition may be evaluated by measuring the transmittance of the composition. A method for determining the transmittance is described in the examples that follow. It is expressed as a percentage. A composition is considered as being clear or limpid if it has a transmittance, for a wavelength of 500 nm, of at least 60%, preferably of at least 70% and even more preferentially of at least 80%.

Other characteristics, advantages and modes of application of the polymer according to the invention will emerge more clearly on reading the description and the examples that follow, which are given as a nonlimiting illustration.

In the text hereinbelow, the expressions "between . . . and . . . ", "ranging from . . . to . . . " and "varying from . . . to . . . " are equivalent and are intended to mean that limits are included, unless otherwise mentioned.

Unless otherwise mentioned, the term "comprising one" should be understood as "comprising at least one".

Description of a Polymer According to the Invention

As indicated previously, the polymer according to the invention obtained by radical polymerization of a mixture of monomers comprises:
  at least one anionic monomer (a) having a polymerizable vinyl group,
  at least one nonionic hydrophobic monomer (b) having a polymerizable vinyl group and
  one or several cross-linking monomer(s) (c) including at least one compound of formula (I):

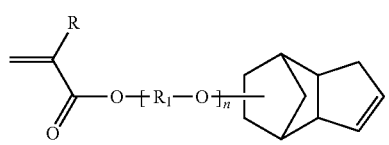

(I)

in which:
  R is a hydrogen atom or a methyl group,
  n is equal to 0 or is an integer from 1 to 30, for example from 1 to 20, or for example from 1 to 15, or for example from 1 to 10, and
  $R_1$ is a $C_1$-$C_{20}$ linear or branched alkyl group.

Preferably according to the invention, the polymer according to the invention does not contain any hydroxylated monomer having a polymerizable vinyl group or else does not contain any monomer having an isocyanate group.

Also preferably according to the invention, the polymer according to the invention is obtained by radical polymerization of a mixture of monomers consisting of:
  at least one anionic monomer (a) having a polymerizable vinyl group,
  at least one nonionic hydrophobic monomer (b) having a polymerizable vinyl group and
  one or several cross-linking monomer(s) (c) including at least one compound of formula (I):

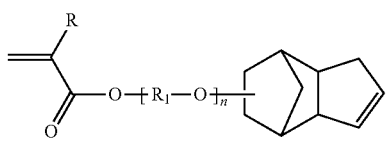

(I)

in which:
  R is a hydrogen atom or a methyl group,
  n is equal to 0 or is an integer from 1 to 30, for example from 1 to 20, or for example from 1 to 15, or for example from 1 to 10, and
  $R_1$ is a $C_1$-$C_{20}$ linear or branched alkyl group.

Also preferably according to the invention, n is an integer from 1 to 30, for example from 1 to 20, or for example from 1 to 15, or for example from 1 to 10.

In the text hereinbelow, the proportions of monomers entering in the composition of the polymer according to the invention are expressed as weight percentages based on the total weight of monomers used to form the polymer.

According to a particular embodiment, the polymer according to the invention does not comprise any monomer unit other than the monomers (a), (b), and (c) (with the exception of the optional presence of fragments of transfer agents or of polymerization initiators).

In other words, according to one embodiment variant, the sum of the contents of monomers (a), (b) and (c) in the composition of the polymer according to the invention is equal to 100%.

According to another embodiment, the polymer according to the invention may also comprise one or several additional monomer unit(s) distinct from the monomers (a), (b) and (c).

In particular, the composition of the polymer according to the invention may also comprise one or several monomer(s) (d) having a polymerizable vinyl group and a hydrophobic hydrocarbon chain and/or one or several additional nonionic monomer(s) (e) as detailed more specifically in the text hereinbelow.

The monomers (a), (b), (c), (d) and (e) in the composition of the polymer according to the invention are different. In particular, said monomer(s) (b) are different from said monomer(s) (d) and/or from said monomer(s) (e).

According to a particular embodiment, the polymer according to the invention is a multiphasic polymer.

For the purposes of the invention, the term "multiphasic polymer" is intended to denote a multiphasic polymer particle, in other words a polymer particle having a nonhomogeneous composition, prepared via a sequential polymerization method in at least two steps from at least two compositions (or mixtures) of distinct monomers.

As will be presented hereinbelow, on conclusion of the first step, a first polymer, referred to hereinbelow as polymer P1, is obtained by radical polymerization from a first mixture of monomers (a), (b) and (c) and optionally (d) and/or (e), and then, at the end of the second step, a second polymer, referred to hereinbelow as polymer P2, is obtained by radical polymerization from a second mixture of monomers (a'), (b') and (c') and optionally (d') and/or (e'). Given that (a') is a nonionic monomer having a polymerizable vinyl group, (b') is a nonionic hydrophobic monomer having a polymerizable vinyl group, (c') is one or several cross-linking monomer(s) optionally including a compound of formula (I), (d') is a monomer having a polymerizable vinyl group and an at least $C_{10}$ hydrophobic hydrocarbon chain (distinct from (b')), and (e') is an optionally nonionic additional monomer (distinct from (b')).

According to this particular embodiment, the multiphasic particles according to the invention may especially be core/shell structured, the first polymer forming the "core" and the second polymer forming the "shell". This "core/shell" name should not, however, be interpreted as denoting a particle in which the "core" part is totally covered or encapsulated with a "shell" part, but as denoting a particle of controlled morphology having two distinct phases.

Thus, for the purposes of the invention, the term "polymer according to the invention" comprises both a polymer obtained by radical polymerization of a single mixture of monomers as defined below, and a multiphasic polymer within the meaning of the present invention, i.e. formed from several polymer compositions including at least one polymer composition P1 and one polymer composition P2 as detailed hereinbelow.

For the purposes of the present invention, the term "polymer composition P1" and the term "polymer P1" are denoted without distinction.

For the purposes of the present invention, the term "polymer composition P2" and the term "polymer P2" are denoted without distinction.

The term "polymer P1" may be understood as a single polymer P1 as defined above or several polymers P1 obtained by sequential polymerization.

Similarly, the term "polymer P2" may be understood as a single polymer P2 as defined above or several polymers P2 obtained by sequential polymerization.

According to a particular embodiment, the polymer P1 does not comprise any monomer units other than the monomers (a), (b) and (c) (with the exception of the optional presence of fragments of transfer agents or of polymerization initiators).

According to a particular embodiment, the polymer P2 does not comprise any monomer units other than the monomers (a'), (b') and (c') (with the exception of the optional presence of fragments of transfer agents or of polymerization initiators).

In other words, according to an embodiment variant, the sum of the contents of monomers (a), (b) and (c) in the composition of the polymer P1 (respectively (a'), (b') and (c') in the composition of the polymer P2) is equal to 100%.

According to another embodiment, the polymer P1 and/or the polymer P2 may also comprise one or several additional monomer unit(s) distinct from the monomers (a), (b) and (c) (respectively (a'), (b') and (c')).

In particular, the composition of the polymer P1 (respectively of the polymer P2) may also comprise one or several monomer(s) (d) (respectively (d')) having a polymerizable vinyl group and a hydrophobic hydrocarbon chain and/or one or several optionally nonionic additional monomer(s) (e) (respectively (e')) as detailed more specifically in the text hereinbelow).

Moreover, it is understood that the monomers (a) and (a') (respectively (b) and (b'), respectively (c) and (c'), respectively (d) and (d'), respectively (e) and (e')) entering in the composition of the polymer P1 and of the polymer P2 may be of the same nature in the polymer P1 and in the polymer P2, or of different nature.

The monomers (a), (b), (c), (d) and (e) in the composition of the polymer P1 are different. In particular, said monomer(s) (b) are different from said monomer(s) (d) and/or from said monomer(s) (e). This is likewise the case for the monomers (a'), (b'), (c'), (d') and (e') in the composition of the polymer P2.

According to a particular embodiment, the polymer P1/polymer P2 weight distribution of the multiphasic polymer according to the invention is between 45/55 and 95/5, in particular between 60/40 and 90/10.

Anionic Monomer Having a Polymerizable Vinyl Group, Known as "Monomer (a)"

According to a particular embodiment, the anionic monomers (a) (and (a')) having a polymerizable vinyl group, referred to more simply in the text hereinbelow as "anionic monomers", comprise at least one carboxylic group.

In particular, the anionic monomers may be chosen from acrylic acid, methacrylic acid, maleic acid, itaconic acid, crotonic acid and their mixtures, and/or the salts of these acids.

According to a particular embodiment, the anionic monomers may be chosen from among acrylic acid and/or methacrylic acid monomers and/or one of their salts.

According to another embodiment, the anionic monomers may be chosen from among acrylic acid and/or methacrylic acid monomers.

Preferably, the anionic monomer of the polymer according to the invention is methacrylic acid (MAA).

Said anionic monomer(s) may represent more than 20% by weight, for example at least 23% by weight, or for example at least 25% by weight, in particular from 25% to 50% by weight, and more particularly from 27% to 41% by weight, based on the total weight of monomers forming the polymer.

According to a particular embodiment, when the polymer according to the invention is a multiphasic polymer:
said anionic monomer(s) (a) may represent more than 20% by weight, for example at least 23% by weight, or for example at least 25% by weight, in particular from 25% to 50% by weight, and more particularly from 27% to 41% by weight, based on the total weight of monomers forming the polymer P1, and
said anionic monomer(s) (a') may represent more than 20% by weight, for example at least 23% by weight, or for example at least 25% by weight, in particular from 25% to 50% by weight, and more particularly from 26% to 35% by weight, based on the total weight of monomers forming the polymer P2.

According to yet another embodiment, the mass proportion of monomer (a') in the polymer P2 (mass content of monomers (a') based on the total weight of monomers forming the polymer P2) is less than that in the polymer P1 (mass content of monomers (a) based on the total weight of monomers forming the polymer P1).

Nonionic Hydrophobic Monomer Having a Polymerizable Vinyl Group, Known as "Monomer (b)"

The nonionic hydrophobic monomers (b) (and (b')) having a polymerizable vinyl group, referred to more simply in the text hereinbelow as "nonionic hydrophobic monomers", are monomers not having any positive charge or any negative charge in aqueous solution.

They may be chosen from among esters, amides or nitriles of acrylic or methacrylic acids or from among acrylonitrile, styrene, methylstyrene, diisobutylene, vinylpyrrolidone or vinylcaprolactam.

Most particularly, the nonionic hydrophobic monomers may be chosen from among $C_1$-$C_8$ alkyl acrylates or $C_1$-$C_8$ alkyl methacrylates, such as methyl acrylate, ethyl acrylate (also known as EA in the text hereinbelow), butyl acrylate, 2-ethylhexyl acrylate, methyl methacrylate, ethyl methacrylate, butyl methacrylate and their mixtures.

According to a particular embodiment, the nonionic hydrophobic monomers may be chosen from among methyl acrylate, ethyl acrylate, butyl acrylate, ethyl methacrylate and their mixtures.

In particular, the nonionic hydrophobic monomer of the polymer according to the invention may be ethyl acrylate.

Said nonionic hydrophobic monomer(s) may represent from 45% to 75% by weight, in particular from 48% to 68% by weight and more particularly from 50% to 64% by weight, based on the total weight of monomers forming the polymer according to the invention.

Said anionic monomer(s) and said nonionic hydrophobic monomer(s) may represent more than 83% by weight, in particular between 83% and 99.8% or between 85% and 99.6% by weight of the overall composition of the polymer of the invention.

The term "overall composition" means the total weight of the monomers used for the synthesis of the polymer according to the invention.

According to a particular embodiment, the polymer according to the invention is such that:
- the anionic monomer is chosen from among acrylic acid and/or methacrylic acid and/or one of their salts; for example, it is chosen from among acrylic acid and/or methacrylic acid; in particular, this monomer is methacrylic acid, and
- the nonionic hydrophobic monomer is chosen from among methyl acrylate, ethyl acrylate, butyl acrylate, ethyl methacrylate and their mixtures, in particular this monomer is ethyl acrylate.

According to a particular embodiment, when the polymer according to the invention is a multiphasic polymer, said nonionic hydrophobic monomer(s) (b) may represent from 45% to 75% by weight, in particular from 48% to 65% by weight and more particularly from 50% to 60% by weight, based on the total weight of monomers forming the polymer P1 and said nonionic hydrophobic monomer(s) (b') may represent from 45% to 75% by weight, in particular from 50% to 68% by weight and more particularly from 55% to 64% by weight, based on the total weight of monomers forming the polymer P2.

According to a particularly preferred embodiment, the mass proportion of monomers (b') in the polymer P2 (mass content of monomers (b') based on the total weight of monomers forming the polymer P2) is greater than that in the polymer P1 (mass content of monomers (b) based on the total weight of monomers forming the polymer P1).

According to one embodiment, the nonionic hydrophobic monomers (b')/anionic monomers (a') weight distribution in the composition of the polymer P2 is between 60/40 and 85/15, in particular between 65/35 and 80/20.

According to a particular embodiment, the nonionic hydrophobic monomers (b)/anionic monomers (a) weight distribution in the composition of the polymer P1 is between 53/47 and 70/30, in particular between 55/45 and 68/32.

Cross-Linking Monomer Including at Least One Compound of Formula (I), Known as "Monomer (c)"

The mixture of monomers compliant with the invention also comprises one or several cross-linking monomer(s) (c) including at least one compound of formula (I) as defined below.

According to a particular embodiment, when the polymer according to the invention is a multiphasic polymer, the mixtures of monomers leading to the polymer P1 and to the polymer P2 both also comprise one or several cross-linking monomer(s) (c) and (c'), respectively, only one of the monomers (c) and (c') comprising at least one compound of formula (I) as defined below. Thus, according to this embodiment, either the mixture of monomers leading to the polymer P1 or the mixture of monomers leading to the polymer P2 comprises a compound of formula (I) as defined below.

According to another particular embodiment, when the polymer according to the invention is a multiphasic polymer, the mixtures of monomers leading to the polymer P1 and to the polymer P2 both also comprise one or several cross-linking monomer(s) (c) and (c'), respectively, each of the monomers (c) and (c') comprising at least one compound of formula (I) as defined below.

The cross-linking monomers (c) and (c') are referred to more simply in the text hereinbelow as "cross-linking monomers".

According to a particular embodiment, the polymer according to the invention comprises as cross-linking monomer only one compound of formula (I).

According to another embodiment, it comprises two different cross-linking monomers including at least one compound of formula (I).

According to yet another embodiment, it comprises three different cross-linking monomers including at least one compound of formula (I).

The cross-linking monomer(s) are used to generate a polymer in the form of a three-dimensional network.

The compound of formula (I) and the optional additional cross-linking monomer(s) are defined below.

(a) Compound of Formula (I)

As presented previously, the mixtures of monomers compliant with the invention necessarily comprise as cross-linking monomer at least one compound of formula (I):

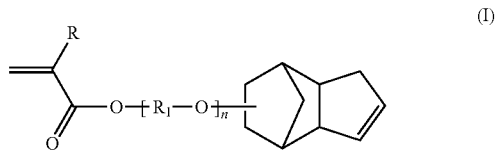

in which:
R is a hydrogen atom or a methyl group,
n is equal to zero or is an integer from 1 to 30, for example from 1 to 20, or for example from 1 to 15, or for example from 1 to 10, and
$R_1$ is a $C_1$-$C_{20}$ linear or branched alkyl group.

It is understood that the ester-ether chain may be linked to the tricyclo[$5.2.1.0^{2.6}$]decenyl ring either via the carbon atom of the tricycle featured above or via the carbon atom of the tricycle located below the bond starting from the oxygen atom of the group —[R1-O]$_n$—.

According to one embodiment, the compound of formula (I) is such that R is a hydrogen atom or a methyl group, $R_1$ is a —$(CH_2)_2$— group, and n is 1.

According to another embodiment, the compound of formula (I) is such that R is a hydrogen atom and n is equal to zero.

According to yet another embodiment, the compound of formula (I) is chosen from among:
ethylene glycol dicyclopentenyl ether methacrylate (also known as ethylene glycol tricyclo[$5.2.1.0^{2.6}$]decene methacrylate, EGDCPEMA, for instance Fancryl FA-512M™ or Fancryl FA-512MT™ sold by the company Hitachi Chemical),
ethylene glycol dicyclopentenyl ether acrylate (also known as ethylene glycol tricyclo[$5.2.1.0^{2.6}$]decene acrylate, EGDCPEA, for instance Fancryl FA-512AS™ sold by the company Hitachi Chemical),
dicyclopentenyl ether acrylate (also known as tricyclo [$5.2.1.0^{2.6}$]decene acrylate, for instance Fancryl FA-511AAS™ sold by the company Hitachi Chemical) and
their mixtures, for example the mixture of EGDCPEA and of EGDCPEMA.

According to yet another embodiment, the compound of formula (I) is EGDCPEA.

According to yet another of its aspects, the present invention relates to the use of a monomer of formula (I):

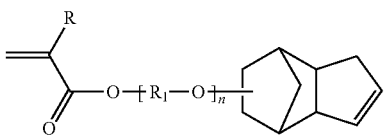

in which:
R is a hydrogen atom or a methyl group,
n is equal to zero or is an integer from 1 to 30, for example from 1 to 20, or for example from 1 to 15, or for example from 1 to 10, and
$R_1$ is a $C_1$-$C_{20}$ linear or branched alkyl group,
in an amount of less than 5% by weight based on the total weight of monomers forming the polymer, to prepare a polymer, in particular to prepare a polymer whose composition is defined above.

The present invention also relates to the use of a monomer of formula (I):

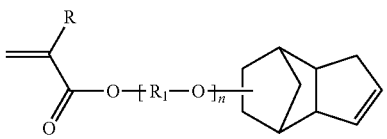

in which:
R is a hydrogen atom or a methyl group,
n is equal to zero or is an integer from 1 to 30, for example from 1 to 20, or for example from 1 to 15, or for example from 1 to 10, and
$R_1$ is a $C_1$-$C_{20}$ linear or branched alkyl group,
in an amount of less than 5% by weight based on the total weight of monomers forming the polymer, to cross-link a polymer/mixture of monomers, in particular to cross-link a mixture of monomers as mentioned above.

(b) Additional Cross-Linking Monomer(s)

As indicated above, the mixtures of monomers compliant with the invention may, besides a compound of formula (I) as cross-linking monomer, also comprise another or several other additional cross-linking monomer(s) (c) distinct from the compound of formula (I) as defined previously.

According to a particular embodiment, the polymer according to the invention comprises only one other cross-linking monomer distinct from the compound of the formula (I).

According to another embodiment, it comprises two different cross-linking monomers, distinct from the compound of formula (I).

According to the present invention, use is made, as additional cross-linking monomer distinct from a compound of formula (I), of a monomer which is a polyunsaturated compound. This compound may comprise two, three or several ethylenic unsaturations.

The additional cross-linking monomer may have hydrophilic, hydrophobic or amphiphilic nature.

Examples of these compounds include di(meth)acrylate compounds such as polyalkylene glycol di(meth)acrylate, especially polypropylene glycol di(meth)acrylate, ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, but also 2,2'-bis(4-(acryloxypropyloxyphenyl)propane, 2,2'-bis(4-(acryloxydiethoxyphenyl)propane and zinc acrylate; tri(meth)acrylate compounds such as trimethylolpropane tri(meth)acrylate and ethoxylated trimethylolpropane tri(meth)acrylate, trimethylolethane tri(meth)acrylate, pentaerythritol tri(meth)acrylate and trimethylolmethane tri(meth)acrylate; tetra(meth)acrylate compounds such as ditrimethylolpropane tetra(meth)acrylate, tetramethylolmethane tetra(meth)acrylate and pentaerythritol tetra(meth)acrylate; hexa(meth)acrylate compounds such as dipentaerythritol hexa(meth)acrylate; penta(meth)acrylate compounds such as dipentaerythritol penta(meth)acrylate; allylic compounds such as allyl (meth)acrylate, diallyl phthalate, diallyl itaconate, diallyl fumarate, diallyl maleate and triallyl cyanurate; polyallyl ethers of sucrose containing from 2 to 8 groups per molecule, polyallyl ethers of pentaerythritol such as pentaerythritol diallyl ether, pentaerythritol triallyl ether and pentaerythritol tetraallyl ether; trimethylolpropane polyallyl ethers such as trimethylolpropane diallyl ether and trimethylolpropane triallyl ether. Other polyunsaturated compounds include divinyl glycol, divinylbenzene, divinylcyclohexyl and methylenebisacrylamide.

According to another aspect, the additional cross-linking monomers may be prepared via an esterification reaction of a polyol with an unsaturated anhydride such as maleic anhydride or itaconic anhydride or via an addition reaction with an isocyanate such as 3-isopropenyldimethylbenzene isocyanate.

Use may also be made of the following compounds to obtain additional cross-linking monomers: polyhaloalkanols such as 1,3-dichloroisopropanol and 1,3-dibromoisopropanol; haloepoxyalkanes such as epichlorohydrin, epibromohydrin, 2-methylepichlorohydrin and epiiodohydrin; polyglycidyl ethers such as 1,4-butanediol diglycidyl ether, glycerol 1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ether, bisphenol A-epichlorohydrin epoxy resin and mixtures.

According to a particular embodiment, the additional cross-linking monomers used in the polymer according to the invention are chosen from trifunctional cross-linking agents.

They may be in particular trimethylolpropane tri(meth)acrylate (TMPTA) or ethoxylated trimethylolpropane tri(meth)acrylate (for instance TMPTA 30E).

According to one embodiment, the mixture of monomers that is suitable for use in the invention also comprises as cross-linking monomer (c) at least one monomer different from the compound of formula (I), chosen from the group consisting of trimethylolpropane tri(meth)acrylate, ethoxylated trimethylolpropane tri(meth)acrylate, ethylene glycol di(meth)acrylate, methylenebisacrylamide, triallyl cyanurate, diallyl phthalate, diallyl maleate and their mixtures.

According to another embodiment, the mixture of monomers compliant with the invention comprises as cross-linking monomers two distinct monomers, namely EGDC-PEA and TMPTA.

According to yet another embodiment, the mixture of monomers compliant with the invention comprises as cross-linking monomers two distinct monomers, namely EGDC-PEA and TMPTA 30E.

Said cross-linking monomer(s) may represent less than 5% by weight, in particular from 0.2% to 4.5%, more particularly from 0.25% to 1.15% by weight, and even more particularly from 0.40% to 1.05% by weight, based on the total weight of monomers forming the polymer according to the invention.

Monomer Having a Polymerizable Vinyl Group and a Hydrophobic Hydrocarbon Chain, Known as "Monomer (d)"

The mixture of monomers compliant with the invention may also comprise at least one monomer (d) (or (d')) having a polymerizable vinyl group and an at least $C_{10}$, preferably $C_{12}$ to $C_{36}$, hydrophobic hydrocarbon chain, which is preferably oxyalkylated, distinct from the monomer (b) (or (b')) if it is the monomer (d')).

These monomers may be more particularly chosen from among monomers of formula (II) below:

$$T\text{-}A\text{-}Z \quad (II)$$

in which:
T represents a polymerizable group allowing the copolymerization of the monomer (d) (or (d')),
A represents a polymeric chain constituted of:
  m units of alkylene oxide of formula —$CH_2CHR_1O$— with $R_1$ representing an alkyl group comprising from 1 to 4 carbons, for example an ethyl or methyl group, and m varying from 0 to 150,
  p units of alkylene oxide of formula —$CH_2CHR_2O$— with $R_2$ representing an alkyl group comprising from 1 to 4 carbons, for example an ethyl or methyl group, and p varying from 0 to 150,
  n units of ethylene oxide with n varying from 0 to 150, or from 10 or 15 to 150, or from 10 or 15 to 100, or from 15 to 50, or from 15 to 30, in which the alkylene oxide units of formula —$CH_2CHR_1O$—, the alkylene oxide units of formula —$CH_2CHR_2O$— and the ethylene oxide units are distributed in blocks, alternating or random and
Z represents a saturated or unsaturated, linear, branched, cyclic or polycyclic, fatty chain of at least 10 carbon atoms, for example a $C_{12}$ to $C_{36}$ chain, optionally comprising one or several heteroatom(s) such as for example O, S, N or P.

According to a preferred embodiment, the sum of m, p and n is not zero.

The term "propoxylated units PO" and "butoxylated units BO" means ethoxylated units bearing on one or other of their carbons a methyl or ethyl radical, respectively. An ethoxylated unit is a —$CH_2$—$CH_2$—O unit.

The term "fatty chain" means an aliphatic hydrocarbon chain of a fatty acid, which is linear, branched, cyclic or polycyclic, comprising at least 10 carbon atoms, for example from 12 to 36 carbon atoms, optionally comprising one or several heteroatom(s) such as for example O, S, N or P.

According to one embodiment, the chain Z is a branched chain comprising 16 carbon atoms.

The end T more particularly represents a radical containing a polymerizable unsaturated group, belonging to the group of acrylic, methacrylic, maleic, itaconic or crotonic esters.

The end T may especially be chosen from among acrylate, methacrylate, allylic, vinyl, methacrylurethane and α,α-dimethyl-m-isopropenyl benzyl urethane groups.

According to one embodiment, the monomer (d) or (d') corresponds to formula (III) below:

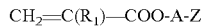

$$CH_2=C(R_1)\text{—}COO\text{-}A\text{-}Z \quad (III)$$

in which:
  $R_1$ represents H or $CH_3$ and
  A and Z have the same definition as in formula (II) above.

According to a particular embodiment, A in the above-mentioned formulae (II) and (III) represents a polymer chain consisting of 15 to 150, in particular from 15 to 50 and especially from 15 to 30 ethylene oxide units.

As examples, the monomer (d) (or (d')) may correspond to formula (II) or (III) in which A and Z are such that:
  m and p are equal to zero, n is equal to 25, $R_1$ represents $CH_3$, Z is a branched chain comprising 16 carbon atoms, namely 2-hexyl-1-decanyl,
  m and p are equal to zero, n is equal to 25, $R_1$ represents $CH_3$, Z is a branched chain comprising 32 carbon atoms,
  m and p are equal to zero, n is equal to 25, $R_1$ represents $CH_3$, Z is a linear chain comprising 22 carbon atoms,
  m and p are equal to zero, n is equal to 36, $R_1$ represents $CH_3$, Z is a branched chain comprising 20 carbon atoms, namely 2-octyl-1-dodecyl, or
  m and p are equal to zero, n is equal to 30, $R_1$ represents $CH_3$, Z is an oxo chain comprising 12 carbon atoms.

According to one particular embodiment, when the polymer according to the invention is a multiphasic polymer, said monomer(s) (d) may be present only in the polymer P1.

According to another particular embodiment, when the polymer according to the invention is a multiphasic polymer, said monomer(s) having a polymerizable vinyl group and a hydrophobic hydrocarbon chain (named (d') in that case) may be present only in the polymer P2.

Alternatively, said monomer(s) (d) and (d') may be present both in the polymer P1 and in the polymer P2 of the multiphasic polymer of the invention.

Said monomer(s) (d), and optionally (d'), may represent from 0 to 20% by weight, in particular from 1 to 15% by weight, and more particularly from 2 to 12% by weight, based on the total weight of monomers forming the polymer according to the invention.

In particular, said monomer(s) (d) may be used in a proportion of at least 0.5% by weight, in particular from 0.5 to 12% by weight, based on the total weight of monomers forming the polymer P1.

In particular, said monomer(s) (d') may be used in a proportion of at least 0.5% by weight, in particular from 0.5 to 12% by weight, based on the total weight of monomers forming the polymer P2.

Optionally Nonionic Additional Monomer, Known as "Monomer (e)"

The mixture of monomers compliant with the invention may also comprise at least one additional monomer (e) (or (e')), which is optionally nonionic, distinct from the monomer (b) (or (b') if it is the monomer (e')).

These optionally nonionic additional monomers (e) and (e') may be chosen more particularly from among:
  2-acrylamido-2-methylpropanesulfonic acid (especially such as the product sold under the name AMPS® by the company Lubrizol) and its salts,
  the unsaturated telomers of acrylic acid,
  the monomers of formula (e1):

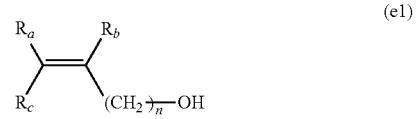

(e1)

in which:
R$_a$, R$_b$ and represent, independently of one another, H or CH$_3$ and
n is an integer equal to 1 or to 2 and
the monomers of formula (e2):

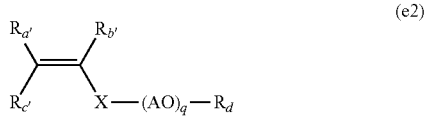

in which:
R$_{a'}$, R$_{b'}$, R$_{c'}$ and R$_{d'}$ represent, independently of one another, H or CH$_3$,
X represents (C=O) or (CH$_2$)$_r$ with r=0, 1 or 2,
(AO) represents a polyalkoxylated chain constituted of alkoxylated units, distributed in blocks, alternating or random, chosen from among the ethoxylated units EO, the propoxylated units PO and the butoxylated units BO and
q is equal to 0 or represents an integer varying from 1 to 150.

In particular, the additional monomers of formula (e1) may be chosen from among allyl alcohol (n=1), methallyl alcohol (n=1) and isoprenol (n=2). For example, the optional monomer is isoprenol.

The term "unsaturated telomers of acrylic acid" means oligomers of acrylic acid or of acryloxypropionic acid, of formula (IV):

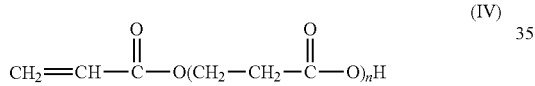

where n is an integer varying from 1 to 10. These various oligomers may be in a mixture. When n=1, the oligomer is an acrylic acid dimer.

It is understood that the various particular embodiments described for each of the anionic monomers, nonionic hydrophobic monomers, cross-linking monomers, monomers having a polymerizable vinyl group and a hydrophobic hydrocarbon chain and optionally nonionic additional monomers of the polymer according to the invention may be combined.

Said optionally nonionic additional monomer(s) (e) and optionally (e') may represent less than 50% by weight, in particular less than 40% by weight and more particularly from 1% to 30% by weight, based on the total weight of monomers forming the polymer according to the invention.

According to a particular embodiment, the polymer according to the invention is obtained from a mixture of monomers comprising at least the following monomers:
one or several anionic monomer(s) chosen from among acrylic acid and/or methacrylic acid and/or one of their salts, preferably acrylic acid and/or methacrylic acid, in particular methacrylic acid,
one or several nonionic hydrophobic monomer(s) chosen from among methyl acrylate, ethyl acrylate, butyl acrylate, ethyl methacrylate and their mixtures, in particular ethyl acrylate,
one or several cross-linking monomer(s) as defined previously including at least one compound of formula (I) chosen from among ethylene glycol dicyclopentenyl ether methacrylate, ethylene glycol dicyclopentenyl ether acrylate, dicyclopentenyl ether acrylate and their mixtures, preferably EGDCPEA, EGDCPEMA and their mixtures, in particular EGDCPEA,
optionally one or several monomer(s) having a polymerizable vinyl group and a hydrophobic hydrocarbon chain as described previously and
optionally one or several optionally nonionic additional monomer(s) as defined previously.

Method for Preparing a Polymer According to the Invention

The polymer according to the invention may be prepared via conventional polymerization techniques starting especially from the monomers (a), (b), (c) and optionally (d), (e) and one or several other cross-linking monomer(s) distinct from a compound of formula (I) as defined previously.

According to one embodiment, the polymer according to the invention may be obtained by emulsion, dispersion or solution radical polymerization.

According to another embodiment, the polymer according to the invention is obtained by emulsion radical polymerization.

Polymerization is carried out in suitable solvents, in the presence of known initiators.

By way of example, the polymerization initiator may be a persulfate salt, such as ammonium persulfate.

The emulsion radical polymerization may be carried out in the presence of at least one surfactant and optionally of at least one chain-transfer agent, for regulating the molecular mass of the chains produced during the polymerization.

As surfactants that may be used, mention may be made of:
anionic surfactants, such as for example a fatty acid salt, an alkyl sulfate salt (such as sodium lauryl sulfate), an alkyl ether sulfate salt (such as sodium lauryl ether sulfate), an alkylbenzenesulfonate salt (such as sodium dodecylbenzenesulfonate), an alkyl phosphate salt or a sulfosuccinate diester salt, a cocoamphoacetate salt (such as sodium cocoamphoacetate), a cocoamphodiacetate salt (such as sodium cocoamphodiacetate), a lauroyl glutamate salt (such as sodium lauroyl glutamate), a cocoyl isethionate salt (such as sodium cocoyl isethionate), a lauroyl methyl isethionate salt (such as sodium lauroyl methyl isethionate), a methyl cocoyl taurate salt (such as sodium methyl cocoyl taurate), a methyl oleyl taurate salt (such as sodium methyl oleyl taurate), a lauroyl sarcosinate salt (such as sodium lauroyl sarcosinate), a laureth-3 sulfosuccinate salt (such as sodium laureth-3 sulfosuccinate), a cocoyl apple amino acid salt (such as sodium cocoyl apple aminate), a cocoyl oat amino acid salt (such as sodium cocoyl oat aminate),
nonionic surfactants, such as for example a polyoxyethylene alkyl ether or a polyoxyethylene fatty acid ester,
cationic surfactants, such as for example quaternary alkyl- and/or aryl-ammonium halides,
zwitterionic or amphoteric surfactants, such as for example surfactants comprising a betaine group, and their mixtures.

As chain-transfer agents, mention may be made advantageously of mercaptan compounds comprising at least four carbon atoms, such as butyl mercaptan, n-octyl mercaptan, n-dodecyl mercaptan and tert-dodecyl mercaptan.

The emulsion polymerization is conventionally carried out in an aqueous dispersion medium.

Thus, according to another of its aspects, the invention relates to a method for the preparation via radical polymerization of a polymer as defined previously, comprising at least the step consisting of polymerizing a mixture of:
- at least one anionic monomer (a) having a polymerizable vinyl group,
- at least one nonionic hydrophobic monomer (b) having a polymerizable vinyl group,
- one or several cross-linking monomer(s) (c) including at least one compound of formula (I):

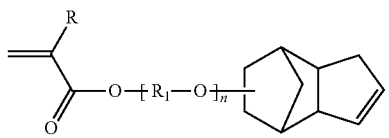

in which:
- R is a hydrogen atom or a methyl group,
- n is equal to 0 or is an integer from 1 to 30, for example from 1 to 20, or for example from 1 to 15, or for example from 1 to 10, and
- $R_1$ is a $C_1$-$C_{20}$ linear or branched alkyl group,
- optionally at least one monomer (d) having a polymerizable vinyl group and an at least $C_{10}$, preferably $C_{12}$ to $C_{36}$, hydrophobic hydrocarbon chain, which is optionally oxyalkylated, distinct from the monomer (b) and
- optionally at least one additional monomer (e) that is optionally nonionic, distinct from the monomer (b).

The polymer of the invention may also be polymerized via an inverse emulsion synthesis.

With this technique, the monomers are dissolved in water, the acidic anionic monomer(s) being optionally partially or totally neutralized. This solution of the monomers is then emulsified in a solvent, for instance a mixture of alkanes or a petroleum fraction, or a mixture of synthetic or natural oils. The synthesis of the polymer is then carried out using water-soluble initiators, allowing polymerization within each emulsion droplet in the continuous oily phase. This technique also makes it possible to obtain polymers with a higher mean molecular mass than via direct emulsion polymerization in water.

The polymer of the invention may also be polymerized via a solvent phase synthesis.

With this technique, the monomers are dissolved in a solvent or mixture of solvents, such as chlorinated solvents, aromatic solvents or other volatile solvents. The polymerization is then carried out using initiators that are soluble in the solvent. The polymer chains precipitate during their growth in the form of a pulverulent solid, which is then separated out by filtration, the residual solvents then being removed by evaporation under vacuum.

This technique also makes it possible to obtain polymers with a higher mean molecular mass than via direct emulsion polymerization in water.

According to a particular embodiment, when the polymer according to the invention is a multiphasic polymer, it may be prepared sequentially, by emulsion, dispersion or solution radical polymerization, preferably in at least two consecutive steps as explained hereinbelow, the first step being as defined previously and allowing the production of a first polymer P1.

Preferably, the multiphasic polymer according to the invention is prepared by radical polymerization in at least two steps, the polymer P1 and the polymer P2 being produced in two sequential emulsion polymerization steps, in particular in this order: P1 and then P2.

The polymerization is carried out under suitable conditions as described previously.

Thus, according to a particular embodiment, a method according to the invention also comprises at least the following subsequent step:
- polymerization, in the presence of the polymer P1 obtained previously at the end of the method as described previously, of a second mixture of monomers allowing the obtention of a second polymer P2 comprising:
  - at least one anionic monomer (a') having a polymerizable vinyl group,
  - at least one nonionic hydrophobic monomer (b') having a polymerizable vinyl group,
  - one or several cross-linking monomer(s) (c') including at least one compound of formula (I):

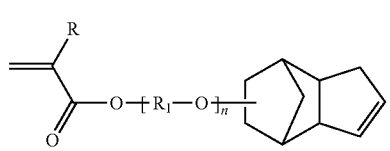

in which:
- R is a hydrogen atom or a methyl group,
- n is equal to 0 or is an integer from 1 to 30, for example from 1 to 20, or for example from 1 to 15, or for example from 1 to 10, and
- $R_1$ is a $C_1$-$C_{20}$ linear or branched alkyl group,
- optionally at least one monomer (d') having a polymerizable vinyl group and an at least $C_{10}$, for example $C_{12}$ to $C_{36}$, hydrophobic hydrocarbon chain, which is optionally oxyalkylated, distinct from the monomer (b') and
- optionally at least one additional monomer (e') that is optionally nonionic, distinct from the monomer (b').

From a practical viewpoint, the first step consists in placing the monomers intended to enter in the composition of the polymer P1 in contact with a polymerization initiator, this placing in contact possibly being carried out in discontinuous mode, or in batch mode, or in semi-batch mode or in semi-continuous mode (the placing in contact being carried out over a period that may range from several minutes to several hours).

From a practical viewpoint, the second step (step of preparing the polymer P2) may take place in the following manner:
- a step of adding the monomers intended to enter in the composition of the polymer P2 to a dispersion medium comprising the already-formed polymer P1, this addition possibly taking place in a discontinuous mode, a batch mode, a semi-batch mode or a semi-continuous mode (the placing in contact being carried out over a period which may range from several minutes to several hours) and
- simultaneously for the semi-continuous mode or subsequent to this addition step for the discontinuous mode, a step of introducing a polymerization initiator.

Applications of a Polymer According to the Invention

The polymers according to the invention prove to be particularly efficient as rheology modifying agents in a wide range of aqueous compositions. Mention may be made of aqueous compositions in varied industrial fields and especially fracking fluids in drilling, ceramic formulations, and paper coating colors. Mention is made in particular of washing compositions containing surfactants, such as personal care or home care compositions.

The term "personal care compositions" comprises, for example, cosmetic compositions, personal hygiene compositions, toiletry products and cleaning compositions for application to the body (including the skin, the hair and the nails) of humans or animals, for example shampoo compositions. The term "home care compositions" includes compositions used for cleaning or maintaining sanitary conditions, for example in the kitchen, the bathroom, detergent products, laundry products, etc.

Thus, according to yet another of its aspects, the invention relates to an aqueous composition comprising at least one polymer according to the invention or as obtained according to the method described above.

The polymer according to the invention may be used in the aqueous composition in a proportion of from 0.1% to 20% by weight, in particular from 0.5% to 12% by weight, based on the total weight of the composition.

As illustrated in the examples that follow, the polymer according to the invention advantageously makes it possible to combine performances in terms of thickening effect, clearness and suspending properties. In other words, it allows the production of an aqueous composition having the desired viscosity and comprising a limpid continuous phase and particles in suspension distributed homogeneously in the continuous phase.

The invention thus more particularly relates to the use of a polymer according to the invention or as obtained according to a method as defined previously in an aqueous composition as a thickening and suspending agent.

Thus, advantageously, the polymer according to the invention may be used in surfactant-rich formulations such as the abovementioned detergent and cosmetic compositions.

The invention also relates to the use for the preparation of a stable aqueous composition, comprising a limpid continuous phase and particles in suspension distributed in the continuous phase, of a polymer as defined previously.

The invention also relates to an agent for obtaining a stable aqueous composition, comprising a limpid continuous phase and particles in suspension distributed in the continuous phase, comprising a polymer according to the invention.

In addition to the clearness it provides, the agent of the invention thus makes it possible to maintain in suspension the particles present in the composition. The use of a composition thus formulated therefore does not require any mixing step, even if the composition has been stored for several weeks, or even several months.

A composition according to the invention may comprise ingredients conventionally used in the formulations mentioned previously. It may comprise one or several active ingredient(s) (or active agent(s)), in any form whatsoever, and irrespective of the field of application of the composition, as indicated previously. The active principle(s) may be dissolved in the continuous phase of the composition and/or they may be in particulate form, which is insoluble in the continuous phase, and constitute all or some of the particles in suspension.

It may comprise one or several surfactant(s), chosen in particular from among anionic, zwitterionic or amphoteric, cationic or nonionic surfactants, and their mixtures.

The invention relates more particularly to an aqueous cosmetic composition, comprising a continuous phase and particles in suspension in the continuous phase, said continuous phase and/or said particles comprising and/or consisting of a cosmetic active principle, said composition comprising a polymer as defined previously.

As active principle(s), it may comprise a washing base for the body and/or the hair.

Advantageously, the rheology modifying agent according to the invention makes it possible to access to the desired viscosity, clearness and suspending effect properties for a wide pH range, of not only acidic, but also neutral or basic pH values.

This wide pH range includes, needless to say, the mean pH value of human skin. The rheology modifying agent according to the invention is thus of major cosmetic interest.

The invention will now be described by means of the examples that follow, which are obviously given as nonlimiting illustrations of the invention.

EXAMPLES

The following abbreviations are used:
MAA: methacrylic acid
EA: ethyl acrylate
MA: monomer (d) of formula (III) in which m and p are equal to zero, n is equal to 25, $R_1$ represents $CH_3$, Z is a branched chain comprising 16 carbon atoms, namely 2-hexyldecanyl
MA1: monomer (d) of formula (III) in which m and p are equal to zero, n is equal to 25, $R_1$ represents $CH_3$, Z is a branched chain comprising 32 carbon atoms, namely 2-tetradecyl-octadecanyl
MA2: monomer (d) of formula (III) in which m and p are equal to zero, n is equal to 25, $R_1$ represents $CH_3$, Z is a linear chain comprising 22 carbon atoms, namely docosyl
MA3: monomer (d) of formula (III) in which m and p are equal to zero, n is equal to 36, $R_1$ represents $CH_3$, Z is a branched chain comprising 20 carbon atoms, namely 2-octyldodecanyl
MA4: monomer (d) of formula (III) in which m and p are equal to zero, n is equal to 30, $R_1$ represents $CH_3$, Z is an oxo chain comprising 12 carbon atoms
FA-512AS (sold by the company Hitachi): ethylene glycol dicyclopentenyl ether acrylate (EGDCPEA)
FA-512MT (sold by the company Hitachi): ethylene glycol dicyclopentenyl ether methacrylate (EGDCPEMA)
FA-511AAS (sold by the company Hitachi): dicyclopentenyl ether acrylate (DCPEA)
SR 351 (sold by the company Sartomer): trimethylolpropane triacrylate (TMPTA)
SR 454 (sold by the company Sartomer): trimethylolpropane triacrylate 30E (TMPTA 30E)
TMPDE 90 (sold by the company Perstorp): trimethylolpropane diallyl ether (TMPDAE)
SR DFM (sold by the company Sartomer): monomethacrylic TMPDAE
SIPOMER® HPM100 (sold by the company Rhodia): nopol methacrylate 100E
VISIOMER® EGDMA SG (sold by the company Evonik): ethylene glycol dimethacrylate (EDMA).

Example of Synthesis of Polymers in a Semi-Batch Method

The protocol for synthesizing the polymer carried out in semi-batch mode is as follows: 432 g of deionized water and 9.29 g of a solution containing 28% by mass of sodium lauryl ether sulfate are placed in a stirred 1 L reactor heated with an oil bath.

The premix comprising the following ingredients:
ethyl acrylate: 196.1 g,
methacrylic acid: 99.67 g,
macromonomer noted as MA: 25.96 g,
EGDCPEA: 1.38 g,
deionized water: 172.5 g and
solution containing 28% of sodium lauryl ether sulfate: 6.47 g is prepared in a beaker.

This premix is stirred so as to form an emulsion.

A solution consisting of 0.1167 g of sodium persulfate and 5 g of deionized water, known as "initiator 1", is prepared.

A solution consisting of 0.3 g of sodium persulfate and 50 g of deionized water, known as "initiator 2", is prepared.

Initiator 1 is injected when the reactor is heated to a temperature of 86° C.+2° C.

Next, the solution of polymerization initiator 2 is injected into the reactor over 2 hours and the monomer premix is injected into the reactor over 2 hours, in parallel.

35 g of water are then added.

The resulting mixture is heated for a further one hour at a temperature of 86° C.±2° C.

The whole is then cooled to room temperature.

Example of Synthesis of Multiphasic Polymers

The protocol for synthesizing the multiphasic polymer is as follows:

430 g of deionized water and 9.29 g of a solution containing 28% by mass of sodium lauryl ether sulfate are placed in a stirred 1 L reactor heated with an oil bath.

The premix P1 comprising the following ingredients:
ethyl acrylate: 131.74 g,
methacrylic acid: 81.86 g,
macromonomer noted as MA: 19.82 g,
EGDCPEA: 1.05 g,
deionized water: 139.1 g and
solution containing 28% of sodium lauryl ether sulfate: 4.93 g is prepared in a beaker.

This premix is stirred so as to form an emulsion.

The premix P2 comprising the following ingredients:
ethyl acrylate: 54.75 g,
methacrylic acid: 26.74 g,
macromonomer noted as MA: 6.14 g,
EGDCPEA: 0.33 g,
deionized water: 42.8 g and
solution containing 28% of sodium lauryl ether sulfate: 1.54 g is prepared in a beaker.

This premix is stirred so as to form an emulsion.

A solution consisting of 0.318 g of sodium persulfate and 5 g of deionized water, known as initiator 1, is prepared.

A solution consisting of 0.269 g of sodium persulfate and 50 g of deionized water, known as initiator 2, is prepared.

Initiator 1 is injected when the reactor is heated to a temperature of 86° C.+2° C.

Next, the solution of polymerization initiator 2 is injected into the reactor over 2 hours and, in parallel, the premix P1 of monomers is injected into the reactor over 90 minutes, followed by the premix P2 over 30 minutes.

35 g of water are then added.

The resulting mixture is heated for a further 1 hour at a temperature of 86° C.+2° C.

The whole is then cooled to room temperature.

All the polymers presented in the examples that follow were synthesized under the conditions described above, varying the compositions of monomers in the monomer premixes.

The composition of the polymer is indicated as a weight percentage of each of the monomers based on the total weight of monomers forming the polymer.

Similarly, when it is a multiphasic polymer, the composition of the polymer P1 and, respectively, that of the polymer P2 is indicated as a weight percentage of each of the monomers based on the total weight of the monomers of P1 and, respectively, of P2.

Evaluation in an Aqueous Formulation

The polymers are tested in an aqueous formulation, having the composition indicated in table 1 below (2.4% or 3% by weight of polymer based on the total weight of the composition).

TABLE 1

| Compounds | Amount (wt. %) |
|---|---|
| Sodium lauryl ether sulfate (SLES) | 9 |
| Cocamidopropyl betaine (CAPB) | 3 |
| Test polymer | 2.4 or 3 |
| Water | qsp 100 |

The pH of the formulation is adjusted to a value of 5, 6 or 7 by adding lactic acid or sodium hydroxide.

Properties Evaluated

The compositions are evaluated for their clearness, viscosity and suspending performances properties.

Clearness

The clearness of the composition is evaluated by measuring the transmittance according to the following protocol:

The measurements are taken on a Genesys 10 UV™ UV spectrometer (Cole Parmer), equipped with Rotilabo-Einmal Kuvetten PS, 4.5 mL cuvettes. In practice, the machine is preheated for 10 minutes before use. A first measurement is first taken using a cuvette filled with 3.8 mL of double-deionized water (the "blank"). The measurement is then taken with a cuvette filled with 3.8 mL of the solution of cosmetic composition to be tested. The transmittance is then measured at a wavelength of 500 nm. The higher the transmittance value, expressed as a percentage, the clearer the cosmetic composition.

As indicated previously, it is considered that at a transmittance value at 500 nm of at least 60%, the composition is limpid.

Viscosity

The viscosity of said formulations is measured using a Brookfield, LVT model viscometer. Before measuring the viscosity, each of the formulations is left to stand for 24 hours at 25° C. The spindle must be centered relative to the aperture of the flask. The viscosity is then measured at 6 rpm (rotations per minute) using the appropriate module. The viscometer is left rotating until the viscosity is stable.

The rheology modifying agent should give a sufficient viscosity to the formulation in which it is used. In general, the viscosity desired for the thickened formulations is greater than 4,000 mPa·s, in particular greater than 6,000 mPa·s and more particularly greater than 8,000 mPa·s.

Suspending Performances

Viscoelasticity measurements are taken on said formulations using a Haake-Mars III rheometer. The Tan($\delta$) and G' variations as a function of the stress □ (sweep from 0 to 1000 dyn/cm$^2$) are measured at 25° C. using 1° cone/plate geometry. The Tan($\delta$) and G' values at 10 dyn/cm$^2$ are extrapolated and the elastic resistance value is deduced from this measurement.

In general, the stability of particles introduced into said formulations is observed for combined values of G'>60 Pa, Tan($\delta$)<0.55 and elastic resistance >70 dyn/cm$^2$.

Example 1: Polymers According to the Invention

The polymers tested, named pol.1 to pol.20, illustrated in tables 2 to 6, are polymers according to the invention which were synthesized according to the protocols detailed above.

More specifically, pol.1 to pol.14 are polymers prepared according to the semi-batch method, whereas the polymers pol.15 to pol.20 are multiphasic polymers.

In particular, it should be noted that:
- pol. 1 and pol.2, given in table 2, are polymers not comprising any monomer (d),
- pol.3 to pol.9 and pol.15 to pol.20, given in tables 2, 3 and 5, are polymers comprising various cross-linking monomers (c) and
- pol.10 to pol.14, given in table 4, are polymers comprising various monomers (d).

TABLE 2

| Polymers tested | | Pol. 1 | Pol. 2 | Pol. 3 | Pol. 4 | Pol. 5 |
|---|---|---|---|---|---|---|
| Overall composition | EA | 64.00 | 63.82 | 62.52 | 62.52 | |
| | MAA | 35.40 | 35.26 | 34.54 | 34.54 | |
| | MA | — | — | 2.04 | 2.04 | |
| | Cross-linking agent (c) | 0.60 EGDCPEA | 0.92 EGDCPEA | 0.90 EGDCPEA | 0.90 EGDCPEMA | 0.90 DCPEA |
| 3% active agent, pH = 7 | G' (Pa) | 97 | 70 | 77 | 91 | |
| | Tan (δ) | 0.36 | 0.40 | 0.54 | 0.54 | |
| | Elastic resistance (dyn/cm$^2$) | 110 | 80 | 110 | 120 | 115 |
| | T(500 nm) (%) | 98 | 96 | 97 | 98 | 93 |
| | Brook. visco. (mPa · s) | 17500 | 8700 | 15400 | 19900 | 18200 |
| 3% active agent, pH = 6 | Brook. visco. (mPa · s) | 25300 | 25700 | 29000 | 29000 | 28500 |
| 3% active agent, pH = 5 | Brook. visco. (mPa · s) | 12200 | 12300 | 16500 | 16500 | 17600 |

TABLE 3

| Polymers tested | | Pol. 6 | Pol. 7 | Pol. 8 | Pol. 9 |
|---|---|---|---|---|---|
| Overall composition | EA | 60.44 | 60.80 | 60.3 | |
| | MAA | 30.91 | 31.10 | 31.00 | 31.00 |
| | MA | 7.80 | 7.80 | 7.80 | 7.80 |
| | Cross-linking agent (c) | 0.85 EGDCPEA | 0.30 EGDCPEA | 0.90 EGDCPEA + TMPTA (50/50) | 0.90 EGDCPEA + TMPTA 3OE (50/50) |
| 2.4% active agent, pH = 6 | G' (Pa) | 120 | 75 | 108 | 126 |
| | Tan (δ) | 0.30 | 0.45 | 0.31 | 0.30 |
| | Elastic resistance (dyn/cm$^2$) | 115 | 120 | 110 | 120 |
| | T(500 nm) (%) | 89 | 95 | 90 | 90 |
| | Brook. visco. (mPa · s) | 17400 | 16400 | 17400 | 19300 |
| 2.4% active agent, pH = 5 | G' (Pa) | 107 | 66 | 105 | 109 |
| | Tan (δ) | 0.30 | 0.44 | 0.31 | 0.30 |
| | Elastic resistance (dyn/cm$^2$) | 110 | 90 | 110 | 110 |
| | T(500 nm) (%) | 85 | 93 | 87 | 87 |
| | Brook. visco. (mPa · s) | 15700 | 14000 | 15100 | 16300 |

TABLE 4

| Polymers tested | | Pol. 10 | Pol. 11 | Pol. 12 | Pol. 13 | Pol. 14 |
|---|---|---|---|---|---|---|
| Overall composition | EA | 60.67 | 60.67 | 60.67 | 60.67 | 60.67 |
| | MAA | 31.10 | 31.10 | 31.10 | 31.10 | 31.10 |
| | Monomer (d) | 7.80 MA | 7.80 MA1 | 7.80 MA2 | 7.80 MA3 | 7.80 MA4 |
| | EGDCPEA | 0.43 | 0.43 | 0.43 | 0.43 | |
| 2.4% active agent, pH = 6 | G' (Pa) | 119 | 109 | 100 | 173 | 92 |
| | Tan (δ) | 0.33 | 0.30 | 0.40 | 0.42 | 0.26 |
| | Elastic resistance (dyn/cm$^2$) | 150 | 110 | 110 | 300 | 100 |

TABLE 4-continued

| | Polymers tested | Pol. 10 | Pol. 11 | Pol. 12 | Pol. 13 | Pol. 14 |
|---|---|---|---|---|---|---|
| | T(500 nm) (%) | 93 | 80 | 94 | 91 | 91 |
| | Brook. visco. (mPa · s) | 19200 | 16000 | 21100 | 45100 | 12300 |
| 2.4% active agent, pH = 5 | G' (Pa) | 97 | 81 | 96 | 149 | 65 |
| | Tan (δ) | 0.34 | 0.26 | 0.34 | 0.33 | 0.29 |
| | Elastic resistance (dyn/cm$^2$) | 130 | 85 | 105 | 220 | 80 |
| | T(500 nm) (%) | 91 | 66 | 91 | 83 | 86 |
| | Brook. visco. (mPa · s) | 16000 | 10300 | 17300 | 32700 | 9800 |

TABLE 5

| | Polymers tested | | Pol. 15 | Pol. 16 |
|---|---|---|---|---|
| Composition P1 | EA | | 60.34 | 60.17 |
| | MAA | | 36.79 | 36.69 |
| | MA | | 2.17 | 2.17 |
| | Cross-linking agent (c) | | 0.70 EGDCPEA | 0.97 EGDCPEMA |
| Composition P2 | EA | | 67.70 | 68.15 |
| | MAA | | 29.20 | 29.40 |
| | MA | | 1.72 | 1.73 |
| | Cross-linking agent (c) | | 1.38 EGDCPEA | 0.72 EGDCPEMA |
| Overall composition | EA | | 62.52 | 62.52 |
| | MAA | | 34.54 | 34.54 |
| | MA | | 2.04 | 2.04 |
| | Cross-linking agent (c) | | 0.90 | 0.90 |
| | Proportion P1 | | 70.40 | 70.60 |
| | Proportion P2 | | 29.60 | 29.40 |
| 3% active agent, pH = 7 | G' (Pa) | | 83 | 68 |
| | Tan (δ) | | 0.51 | 0.51 |
| | Elastic resistance (dyn/cm$^2$) | | 115 | 95 |
| | T(500 nm) (%) | | 97 | 97 |
| | Brook. visco. (mPa · s) | | 17100 | 20400 |
| 3% active agent, pH = 6 | Brook. visco. (mPa · s) | | 29700 | 29500 |
| 3% active agent, pH = 5 | Brook. visco. (mPa · s) | | 13300 | 14600 |

TABLE 6

| | Polymers tested | Pol. 17 | Pol. 18 | Pol. 19 | Pol. 20 |
|---|---|---|---|---|---|
| Composition P1 | EA | 55.92 | 56.16 | 55.92 | 55.92 |
| | MAA | 35.00 | 35.16 | 35.00 | 35.00 |
| | MA | 8.19 | 8.23 | 8.19 | 8.19 |
| | Cross-linking agent (c) | 0.89 EGDCPEA | 0.45 EGDCPEA | 0.89 EGDCPEMA | 0.89 DCPEA |
| Composition P2 | EA | 62.00 | 62.23 | 62.00 | 62.00 |
| | MAA | 30.50 | 30.61 | 30.50 | 30.50 |
| | MA | 6.76 | 6.79 | 6.76 | 6.76 |
| | Cross-linking agent (c) | 0.74 EGDCPEA | 0.38 EGDCPEA | 0.74 EGDCPEMA | 0.74 DCPEA |
| Overall composition | EA | 57.58 | 57.82 | 57.58 | 57.58 |
| | MAA | 33.77 | 33.92 | 33.77 | 33.77 |
| | MA | 7.80 | 7.83 | 7.80 | 7.80 |
| | Cross-linking agent (c) | 0.85 | 0.43 | 0.85 | 0.85 |
| | Proportion P1 | 72.74 | 72.72 | 72.74 | 72.74 |
| | Proportion P2 | 27.26 | 27.28 | 27.26 | 27.26 |
| 2.4% active agent, pH = 6 | G' (Pa) | 94 | 141 | 97 | 73 |
| | Tan (δ) | 0.29 | 0.28 | 0.30 | 0.47 |
| | Elastic resistance (dyn/cm$^2$) | 85 | 150 | 100 | 75 |
| | T(500 nm) (%) | 78 | 88 | 81 | 94 |
| | Brook. visco. (mPa · s) | 11800 | 19500 | 13200 | 8700 |
| 2.4% active agent, pH = 5 | G' (Pa) | 140 | 139 | 144 | 121 |
| | Tan (δ) | 0.25 | 0.25 | 0.24 | 0.25 |
| | Elastic resistance (dyn/cm$^2$) | 120 | 150 | 130 | 120 |
| | T(500 nm) (%) | 69 | 80 | 69 | 65 |
| | Brook. visco. (mPa · s) | 14600 | 18700 | 15300 | 13500 |

The results presented in tables 2 to 6 show that the polymers according to the invention not only have good properties in terms of thickening, but also make it possible to obtain formulations that have good suspending performances and high clearness for all of the polymers tested.

In addition, the results given in table 3 for pol.8 and pol.9 show that it is possible to use an additional cross-linking monomer (c), in the present case TMPTA or TMPTA 30E, in addition to a compound of formula (I), in the present case EGDCPEA.

Example 2: Polymers Outside the Invention

The polymers tested, named C1 to C9, illustrated in tables 7 to 10, are polymers outside the invention which were synthesized according to the protocols detailed above and which comprise cross-linking monomers not in accordance with those used in the present invention. More particularly, the polymers C1 to C6 are polymers prepared according to the semi-batch method, whereas the polymers C7 to C9 are multiphasic polymers.

TABLE 7

| Polymers tested | | C1 outside the invention | C2 outside the invention | C3 outside the invention |
|---|---|---|---|---|
| Overall composition | EA | 63.54 | 62.52 | 62.52 |
| | MAA | 35.56 | 34.54 | 34.54 |
| | MA | — | 2.04 | 2.04 |
| | Cross-linking agent (c) | 0.90 TMPTA + TMPDAE (75/25) | 0.90 TMPTA | 0.90 TMPTA + monomethacrylic TMPDAE (63/37) |
| 3% active agent, pH = 7 | G' (Pa) | 29 | 44 | 49 |
| | Tan (δ) | 0.56 | 0.90 | 0.58 |
| | Elastic resistance (dyn/cm²) | 30 | 55 | 40 |
| | T(500 nm) (%) | 92 | 98 | 97 |
| | Brook. visco. (mPa · s) | 5100 | 14000 | 9100 |
| 3% active agent, pH = 6 | Brook. visco. (mPa · s) | 23600 | 8800 | 24300 |
| 3% active agent, pH = 5 | Brook. visco. (mPa · s) | 14500 | 5300 | 14400 |

TABLE 8

| Polymers tested | | C4 outside the invention | C5 outside the invention |
|---|---|---|---|
| Overall composition | EA | 62.52 | 62.52 |
| | MAA | 34.54 | 34.54 |
| | MA | 2.04 | 2.04 |
| | Cross-linking agent (c) | 0.90 5-vinyl-2-norbornene | 0.90 nopol methacrylate 10 OE |
| 3% active agent, pH = 7 | G' (Pa) | 52 | 55 |
| | Tan (δ) | 1.23 | 1.88 |
| | Elastic resistance (dyn/cm²) | 40 | 120 |
| | T(500 nm) (%) | 95 | 99 |
| | Brook. visco. (mPa · s) | 3800 | 20100 |

TABLE 8-continued

| Polymers tested | | C4 outside the invention | C5 outside the invention |
|---|---|---|---|
| 3% active agent, pH = 6 | Brook. visco. (mPa · s) | 8220 | 1530 |
| 3% active agent, pH = 5 | Brook. visco. (mPa · s) | 4880 | 2970 |

TABLE 9

| Polymers tested | | C6 outside the invention |
|---|---|---|
| Overall composition | EA | 60.44 |
| | MAA | 30.91 |
| | MA | 7.80 |
| | Cross-linking agent (c) | 0.85 TMPTA |
| 2.4% active agent, pH = 6 | G' (Pa) | 42 |
| | Tan (δ) | 0.58 |
| | Elastic resistance (dyn/cm²) | 50 |
| | T(500 nm) (%) | 94 |
| | Brook. visco. (mPa · s) | 12400 |
| 2.4% active agent, pH = 5 | G' (Pa) | 32 |
| | Tan (δ) | 0.58 |
| | Elastic resistance (dyn/cm²) | 40 |
| | T(500 nm) (%) | 92 |
| | Brook. visco. (mPa · s) | 10800 |

TABLE 10

| Polymers tested | | | C7 outside the invention | C8 outside the invention | C9 outside the invention |
|---|---|---|---|---|---|
| Composition P1 | EA | | 55.92 | 55.92 | 55.92 |
| | MAA | | 35.00 | 35.00 | 35.00 |
| | MA | | 8.19 | 8.19 | 8.19 |
| | Cross-linking agent (c) | | 0.89 EDMA | 0.89 Tricyclodecane dimethanol dimethacrylate | 0.89 5-vinyl-2-norbornene |
| Composition P2 | EA | | 62.00 | 62.00 | 62.00 |
| | MAA | | 30.50 | 30.50 | 30.50 |
| | MA | | 6.76 | 6.76 | 6.76 |
| | Cross-linking agent (c) | | 0.74 EDMA | 0.74 Tricyclodecane dimethanol dimethacrylate | 0.74 5-vinyl-2-norbornene |
| Overall composition | EA | | 57.58 | 57.58 | 57.58 |
| | MAA | | 33.77 | 33.77 | 33.77 |
| | MA | | 7.80 | 7.80 | 7.80 |
| | Cross-linking agent (c) | | 0.85 EDMA | 0.85 Tricyclodecane dimethanol dimethacrylate | 0.85 5-vinyl-2-norbornene |
| Proportion P1 | | | 72.74 | 72.74 | 72.74 |
| Proportion P2 | | | 27.26 | 27.26 | 27.26 |
| 2.4% active agent, pH = 6 | G' (Pa) | | 28 | 26 | Not determinable |
| | Tan (δ) | | 0.71 | 0.78 | Not determinable |
| | Elastic resistance (dyn/cm²) | | 40 | 40 | Not determinable |
| | T(500 nm) (%) | | 95 | 97 | 55 |
| | Brook. visco. (mPa · s) | | 7900 | 8100 | 1100 |

TABLE 10-continued

| Polymers tested | | C7 outside the invention | C8 outside the invention | C9 outside the invention |
|---|---|---|---|---|
| 2.4% active agent, pH = 5 | G' (Pa) | 28 | 25 | Not determinable |
| | Tan (δ) | 0.65 | 0.68 | Not determinable |
| | Elastic resistance (dyn/cm²) | 40 | 35 | Not determinable |
| | T(500 nm) (%) | 94 | 95 | 45 |
| | Brook. visco. (mPa · s) | 9000 | 8700 | 3100 |

In general, the results given in tables 7 to 10 show that the properties of the polymers (thickening effect, suspending performances and clearness) vary according to the nature of the cross-linking monomer used not compliant with the invention.

Certain comparisons, by way of example, are illustrated in the following section.

For example, by comparing compliant pol.6 (EGDCPEA) and non-compliant C6 (TMPTA), it is observed that the formulation comprising pol.6 has better suspending properties (significantly higher G' value and lower Tan (δ) value), a clearness of the same order of magnitude and viscosity values that are higher overall than a formulation comprising C6 or TMPTA.

By comparing compliant pol.2 (EGDCPEA) and non-compliant C1 (TMPTA+TMPDAE (75/25)), it is observed that the formulation comprising pol.2 has better suspending properties, and also a clearness and viscosity values of the same order of magnitude at pH 6 and 5 compared to a formulation comprising C1 or TMPTA/TMPDAE.

By comparing compliant pol.3, pol.4, pol.5, pol.15 or pol.16 with non-compliant C2 or C3, it is observed that the formulations comprising the compliant polymers have better suspending properties and a clearness of the same order of magnitude.

By comparing compliant pol.3, pol.4, pol.5, pol.15 or pol.16 with non-compliant C4, it is observed that the formulations comprising the compliant polymers have higher viscosity values.

By comparing compliant pol.17, pol.19 or pol.20 with non-compliant C7 or C8, it is observed that the formulations comprising the compliant polymers have better suspending properties, a higher viscosity and a clearness of the same order of magnitude.

Finally, by comparing compliant pol.17, pol.19 or pol.20 with non-compliant C9, it is observed that the formulations comprising the compliant polymers have better clearness and a higher viscosity.

Example 3: Ultra-Mild Scrubbing Shower Gel

This example illustrates the use of agents according to the invention in cosmetic formulations of ultra-mild shower gel type, and serves to demonstrate the rheological properties (suspension and viscosity) and organoleptic properties afforded according to the invention.

Thus, using a shower gel formulation based on anionic and zwitterionic surfactants, the composition of which is given in table 11, the aim consisted in checking in this formulation the clearness, the viscosity and the suspension as influenced by various rheology modifying agents including reference products and those according to the invention.

TABLE 11

| | |
|---|---|
| 1-DI water (double-deionized water) | qsp 100 |
| 2-Texapon ® NSO UP (BASF) | 32.14 |
| 3-Dehyton ® PK 45 (BASF) | 6.67 |
| 4-Rheology modifying agent | Polymer tested at 3% |
| 5-Sodium hydroxide | qs pH = 7.0 ± 0.1 |
| 6-Potassium sorbate (Nutrinova) | 0.40 |
| 7-Strawberry Fragrance (Hyteck) | 0.50 |
| 8-Exfoson ® Quin 300 red, exfoliant particles (Soniam) | 2.00 |

Protocol for Preparing the Formulation:

The double-deionized water (1) is introduced in a beaker, and the various ingredients (2) and (3) are then added with stirring.

After homogenization is complete, the rheology modifying agent (4) is added with very moderate stirring.

The pH is measured, and is then adjusted to 7.0±0.1 with the ingredient (5).

After checking the pH, the preserving agent (6) and the fragrance (7) are mixed with moderate stirring into the shower gel formulation.

Finally, the quinoa exfoliant particles (8) are dispersed with stirring.

Table 12 collates all of the rheology modifying agents that were used as ingredient (4) in the context of the tests of the present example 3.

In table 12:
REF: REFerence/INV: INVention/OINV: Outside INVention.

TABLE 12

| | REF NaCl | INV Pol. 15 | OINV C3 |
|---|---|---|---|
| Brookfield viscosity 6 rpm (mPa · s) | 17,800 | 17,100 | 9,100 |
| Tan (δ) | 12 | 0.51 | 0.58 |
| Elastic resistance (dyn/cm²) | 0 | 115 | 40 |
| T(500 nm) (%) | 98 | 97 | 97 |

The invention claimed is:

1. A polymer obtained by radical polymerization of a mixture of monomers comprising:
   (a) at least one anionic monomer (a) having a polymerizable vinyl group;
   (b) at least one nonionic hydrophobic monomer (b) having a polymerizable vinyl group; and
   (c) at least one cross-linking monomer (c) comprising at least one compound of formula (I):

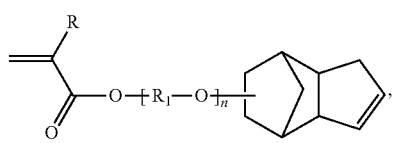

wherein:
R is a hydrogen atom or a methyl group;
n is 1; and
$R_1$ is a $C_1$-$C_{20}$ linear or branched alkyl group.

2. The polymer according to claim 1, wherein:
$R_1$ is a —$(CH_2)_2$— group.

3. The polymer according to claim 1, wherein the mixture of monomers further comprises:

(d) at least one monomer (d) having a polymerizable vinyl group and an at least $C_{10}$ hydrophobic hydrocarbon chain, the monomer (d) being distinct from the monomer (b).

4. The polymer according to claim 1, wherein the mixture of monomers further comprises:
(e) at least one additional monomer (e) that is optionally nonionic, the additional monomer (e) being distinct from the monomer (b).

5. The polymer according to claim 1, wherein the at least one anionic monomer (a) is selected from the group consisting of acrylic acid, a salt of acrylic acid, methacrylic acid, a salt of methacrylic acid, and a mixture thereof.

6. The polymer according to claim 1, wherein the at least one anionic monomer (a) represents more than 20% by weight, based on a total weight of monomers forming the polymer.

7. The polymer according to claim 1, wherein the at least one nonionic hydrophobic monomer (b) is selected from the group consisting of a $C_1$-$C_8$ alkyl acrylate, a $C_1$-$C_8$ alkyl methacrylate, and a mixture thereof.

8. The polymer according to claim 1, wherein the at least one nonionic hydrophobic monomer (b) represents from 45% to 75% by weight, based on a total weight of monomers forming the polymer.

9. The polymer according to claim 1, wherein the mixture of monomers further comprises, as the cross-linking monomer (c), at least one monomer, which is different from the compound of formula W and selected from the group consisting of trimethylolpropane tri(meth)acrylate, ethoxylated trimethylolpropane tri(meth)acrylate, ethylene glycol di(meth)acrylate, methylenebisacrylamide, triallylcyanurate, diallylphtalate, diallylmaleate, and a mixture thereof.

10. The polymer according to claim 1, wherein the at least one cross-linking monomer (c) represents less than 5% by weight, based on a total weight of monomers forming the polymer.

11. The polymer according to claim 3, wherein the at least one monomer (d) comprises a monomer of formula (II):

T-A-Z    (II)

wherein:
T represents a polymerizable group allowing copolymerization of the monomer (d);
A represents a polymeric chain comprising:
m units of alkylene oxide of formula —CH$_2$CHR$_1$O— with R$_1$ representing an alkyl group comprising from 1 to 4 carbons, and m varying from 0 to 150,
p units of alkylene oxide of formula —CH$_2$CHR$_2$O— with R$_2$ representing an alkyl group comprising from 1 to 4 carbons, and p varying from 0 to 150,
n units of ethylene oxide with n varying from 0 to 150, in which the alkylene oxide units of formula —CH$_2$CHR$_1$O—, the alkylene oxide units of formula —CH$_2$CHR$_2$O—, and the ethylene oxide units are distributed in blocks, alternating or random; and
Z represents a saturated or unsaturated, linear, branched, cyclic or polycyclic, fatty chain of at least 10 carbon atoms, optionally comprising at least one heteroatom.

12. The polymer according to claim 3, wherein the at least one monomer (d) represents from 0 to 20% by weight, based on a total weight of monomers forming the polymer.

13. The polymer according to claim 4, wherein the additional monomer (e) is selected from the group consisting of:
2-acrylamido-2-methylpropanesulfonic acid and a salt thereof, an unsaturated telomer of acrylic acid,
a monomer of formula (e1):

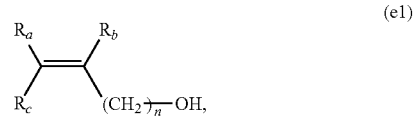

wherein:
$R_a$, $R_b$ and $R_c$ represent, independently of one another, H or CH$_3$, and
n is an integer equal to 1 or to 2, and
a monomer of formula (e2):

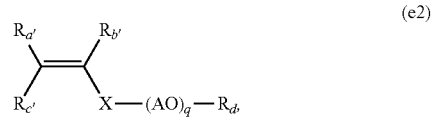

wherein:
$R_{a'}$, $R_{b'}$, $R_{c'}$ and $R_{d'}$ represent, independently of one another, H or CH$_3$,
X represents (C=O) or (CH$_2$)$_r$ with r=0, 1 or 2,
(AO) represents a polyalkoxylated chain comprising alkoxylated units, distributed in blocks, alternating or random, selected from the group consisting of ethoxylated units EO, propoxylated units PO and butoxylated units BO, and
q is equal to 0 or represents an integer varying from 1 to 150.

14. A method for preparing, by radical polymerization, the polymer of claim 1, the method comprising polymerizing a mixture of:
the at least one anionic monomer (a),
the at least one nonionic hydrophobic monomer (b),
the at least one cross-linking monomer (c),
optionally at least one monomer (d) having a polymerizable vinyl group and an at least $C_{10}$ hydrophobic hydrocarbon chain, the at least one monomer (d) being distinct from the monomer (b), and
optionally at least one additional monomer (e) that is optionally nonionic, the monomer (e) being distinct from the monomer (b).

15. The method according to claim 14, further comprising:
polymerizing, in the presence of the polymer, a second mixture of monomers comprising:
at least one anionic monomer (a') having a polymerizable vinyl group,
at least one nonionic hydrophobic monomer (b') having a polymerizable vinyl group,
at least one cross-linking monomer (c') comprising at least one compound of formula

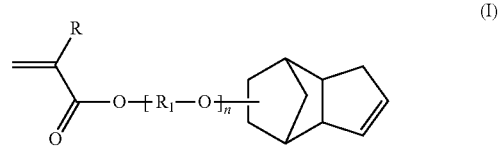

wherein:
R is a hydrogen atom or a methyl group,
n is equal to 0 or is an integer from 1 to 30 and
$R_1$ is a $C_1$-$C_{20}$ linear or branched alkylene group,
optionally at least one monomer (d') having a polymerizable vinyl group and an at least $C_{10}$ hydrophobic hydrocarbon chain, the monomer (d') being distinct from the monomer (b'), and
optionally at least one additional monomer (e') that is optionally nonionic, the additional monomer (e') being distinct from the monomer (b'),
to obtain a second polymer.

16. An aqueous composition, comprising at least one polymer of claim 1.

17. A method, comprising
polymerizing at least one monomer to obtain a polymer, wherein
the at least one monomer comprises a compound of formula (I):

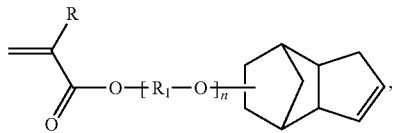

wherein:
R is a hydrogen atom or a methyl group;
n is 1;
$R_1$ is a $C_1$-$C_{20}$ linear or branched alkylene group; and
an amount of the compound of formula (I) is less than 5% by weight, based on a total weight of the at least one monomer.

* * * * *